United States Patent [19]

Obayashi

[11] Patent Number: 5,354,891
[45] Date of Patent: Oct. 11, 1994

[54] METHOD OF PRODUCING AROMATIC AMINE DERIVATIVES

[75] Inventor: Tatsuhiko Obayashi, Kanagawa, Japan

[73] Assignee: Fuji Photo Film Co., Ltd., Kanagawa, Japan

[21] Appl. No.: 26,007

[22] Filed: Mar. 4, 1993

[30] Foreign Application Priority Data

Mar. 5, 1992 [JP] Japan .................................. 4-083152

[51] Int. Cl.$^5$ ........................................ C07C 209/40
[52] U.S. Cl. ................................. 564/394; 548/516; 564/124; 564/130; 564/167; 564/239; 564/414; 564/428; 564/443
[58] Field of Search ............... 564/414, 239, 124, 167, 564/394, 130, 428, 443; 548/516

[56] References Cited

U.S. PATENT DOCUMENTS 3,711,551  1/1973  McMahon .......................... 260/575
4,525,590  6/1985  Rasshofer et al. .................. 544/222
5,196,601  3/1993  Kitsuki et al. ..................... 568/817

OTHER PUBLICATIONS

H. R. Snyder et al. J. of Am. Chem. Soc., vol. 75, p. 2014 (1953).
D. G. Hoare et al, J. of Am. Chem. Soc., vol. 90, No. 6, pp. 1638–1643, (1968).
S. Bittner et al, Tetrahedron Letters, No. 23, pp. 1965–1968, (1974).

*Primary Examiner*—Richard L. Raymond
*Assistant Examiner*—Brian M. Burn
*Attorney, Agent, or Firm*—Birch, Stewart, Kolasch & Birch

[57] ABSTRACT

Disclosed is a method for producing aromatic amine derivatives in a high yield at a low price, which comprises inducing an aromatic hydroxamic acid derivative to undergo a rearrangement reaction under a mild condition in the presence of a base and a nitrile or a nitrile equivalent.

17 Claims, No Drawings

METHOD OF PRODUCING AROMATIC AMINE DERIVATIVES

FIELD OF THE INVENTION

The present invention relates to a method of producing aromatic amine derivatives and, more particularly, to a method of producing aromatic amine derivatives from aromatic hydroxamic acid derivatives.

BACKGROUND OF THE INVENTION

Aromatic amine derivatives are used for ballast groups on photographic couplers, and also useful as intermediates in the syntheses of various functional compounds.

A known method of synthesizing such aromatic amine derivatives is shown below as Route (1), wherein a Lossen rearrangement is utilized (as presented, e.g., by Y. H. Yale et al. in *Chem. Rev.*, vol. 33, p. 209 (1943)).

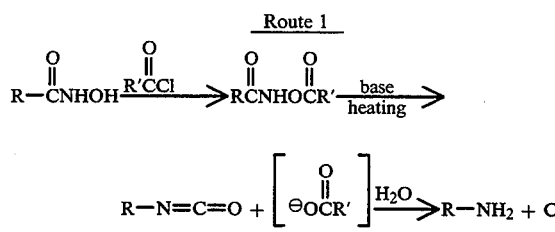

In the above formulae, R and R' each represents an alkyl group or an aryl group.

In the Lossen rearrangement reaction, it is generally necessary in order for the reaction to proceed smoothly, that the reaction take place under relatively mild conditions, and that the hydroxyl group of hydroxamic acid be changed in advance to a desirable splitting-off group (e.g., by acylation) before undergoing the reaction under basic condition (as reported, e.g., by W. B. Renfrow et al. in *J. Am. Chem. Soc.*, vol. 59, p. 2308 (1937), by M. A. Stolberg et al. in ibid., vol. 77, p. 765 (1955), and by R. Swidler et. al. in ibid., vol. 78, p. 3594 (1956)).

On the other hand, it is known that the rearrangement can proceed without a previous acylation of hydroxamic acid when heating is carried out in the presence of an acid catalyst such as polyphosphoric acid. Specifically, the reaction requires a high temperature of about 160° C. (as reported, e.g., by H. R. Snyder et al. in *J. Am. Chem. Soc.*, vol, 75, p. 2014 (1953)).

Also, attempts to omit the process of acylating hydroxamic acid under mild conditions were made by D. G. Hoare et al. and S. Bittner et al. Specifically, D. G. Hoare et al. reported that the reaction proceeded smoothly at room temperature by adding excess 1-benzyl-3-dimethyl-aminopropylcarbodiimide to a weakly acidified aqueous solution containing hydroxamic acid (*J. Am. Chem. Soc.*, vol. 90, p. 1638 (1968)). S. Bittner et al. reported that the reaction proceeded smoothly at room temperature under neutral condition by adding triphenylphosphine and diethylazodicarboxylate in amounts equimolar with hydroxamic acid (*Tetrahedron Letters*, vol. 23, p. 1965 (1974)).

The foregoing method which comprises heating hydroxamic acid in the presence of an acid catalyst such as polyphosphoric acid can avoid an acylation process step, but has the drawback that a high temperature of about 160° C. is required for the reaction to proceed, and the acid catalyst polyphosphoric acid is difficult to handle due to its high viscosity.

Using to the methods proposed by D. G. Hoare et al. and S. Bittner et al., the intended compounds can be obtained under mild conditions while avoiding an acylation process step. However, such methods cannot necessarily be said to ensure a cheap production of the designed compounds, considering the price and type of reagents used.

Therefore, it is desirable that a method be provided for producing aromatic amine derivatives in a high yield from generally inexpensive reagents, under mild conditions without needing an acylation step.

SUMMARY OF THE INVENTION

As a result of various attempts for overcoming drawbacks associated with conventional methods, we have discovered that aromatic amine derivatives can be produced from aromatic hydroxamic acid derivatives in a high yield through a Lossen type rearrangement reaction that is carried out using as a catalyst a small amount of base and a specific nitrile or nitrile equivalent under mild conditions (e.g., such that the reaction temperature is about 60° C.) without using a previous acylation step.

That is, the present invention provides a method of producing an aromatic amine derivative represented by the following formula (I), wherein an aromatic hydroxamic acid derivative represented by the following general (II) undergoes a rearrangement reaction in the presence of a base and a nitrile represented by the following formula (III) or a nitrile equivalent represented by the following formula (IV):

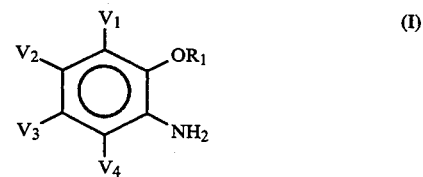

wherein $R_1$ represents an optionally substituted alkyl group, an optionally substituted alkenyl group, an optionally substituted alkynyl group or an optionally substituted aryl group; $V_1$, $V_2$, $V_3$ and $V_4$ each represents a hydrogen atom or a group by which hydrogens on an aromatic ring can be replaced; and further, $V_1$, and $V_2$, $V_2$ and $V_3$, or $V_3$ and $V_4$ may combine with each other to complete a condensed ring;

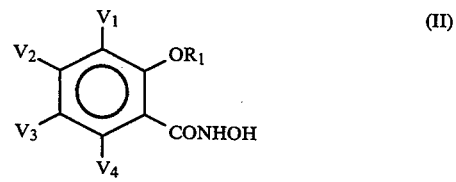

wherein $R_1$, $V_1$, $V_2$, $V_3$ and $V_4$ have the same meanings as defined in formula (I), respectively;

wherein $R_2$ represents an optionally substituted alkyl group or an optionally substituted aryl group; $R_3$ represents an optionally substituted alkyl group or an optionally substituted aryl group; and X represents an alkoxy group, an aryloxy group or a halogen atom.

DETAILED DESCRIPTION OF THE INVENTION

A reaction encompassed by the present invention is thought to proceed, as illustrated by the following route 2, by addition of the hydroxyl group of hydroxamic acid to a nitrile:

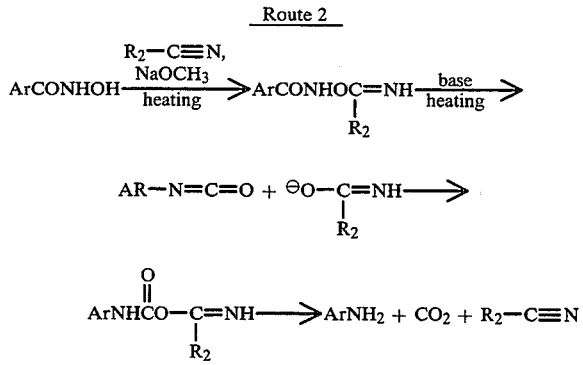

(wherein Ar represents the aryl moiety of formula (II)).

In our inventive process a nitrile not only plays a role corresponding to an acylating agent in a conventional method as shown by the foregoing route 1 but also functions catalytically (by reproduction) in the reaction system.

The compounds represented by formulas (I) and (II) respectively are described below in detail.

When $R_1$ represents an alkyl, alkenyl or alkynyl group in general formulas (I) and (II), it includes alkyl groups containing 1 to 32 carbon atoms, preferably 1 to 22 carbon atoms, and alkenyl and alkynyl groups containing 2 to 32 carbon atoms, preferably 2 to 22 carbon atoms; any of which groups may be substituted or unsubstituted, and which may have a straight-chain, branched chain, or cyclic form. When $R_1$ is an aryl group, it is a substituted or unsubstituted aryl group containing 6 to 20 carbon atoms. In case of $R_1$ being a substituted alkyl, olefinic, acetylenic or aryl group, examples of a substituent suitable therefor include a halogen atom, an alkoxy group, an aryloxy group, a heterocyclyloxy group, an acyloxy group, an alkyl group, an alkenyl group, an alkinyl group, an aryl group, an amino group, a hydroxyl group, a carbonamido group, a sulfonamido group, an ureido group, a sulfamido group, an oxycarbonamido group, a carboxyl group, a carbamoyl group, an oxycarbonyl group, a sulfo group, a sulfamoyl group, an alkylsulfonyl group, an arylsulfonyl group, a cyano group, a nitro group and a heterocyclyl group.

$V_1$, $V_2$, $V_3$ and $V_4$ may be the same or different from one another, and it is preferable that each of them represent a hydrogen atom, a halogen atom, an alkyl group, an alkenyl group, an azyl group, an alkoxy group, an aryloxy group, an acyloxy group, an amido group, a sulfonamido group, an ureido group, an alkyloxycarbonyl group, a carbamoyl group, a sulfamoyl group, a sulfonyl group, a sulfo group, a cyano group or a heterocyclyl group, with a hydrogen atom being particularly preferred. These groups each may further have substituents.

On the other hand, a condensed ring may be formed by combining $V_1$ with $V_2$, $V_2$ with $V_3$, or $V_3$ with $V_4$. Suitable examples of a ring formed by such a combination include substituted and unsubstituted benzene, cyclopentadiene, tropilidene, pyridine, furan, thiophene, pyrrole, thiazole, oxazole, imidazole and triazole rings, with a substituted or unsubstituted benzene being preferred. Suitable examples of substituents these rings can have include those given as preferred examples for $V_1$, $V_2$, $V_3$ and $V_4$.

In the compounds represented by general formula (III), $R_2$ represents a substituted or unsubstituted alkyl group preferably having 1 to 10 carbon atoms, more preferably 1 to 4 carbon atoms, or a substituted or unsubstituted aryl group preferably having 6 to 22 carbon atoms, such as methyl, phenyl, p-nitrophenyl, and the like. In the compounds represented by general formula (IV), $R_3$ has the same meaning as $R_2$ has in the compounds represented by general formula (III). A group represented by X in general formula (IV) is an alkoxy group preferably having 1 to 3 carbon atoms, an aryloxy group or a halogen atom, such as methoxy, phenoxy, chlorine or the like.

The present inventive production method is illustrated in the following reaction scheme.

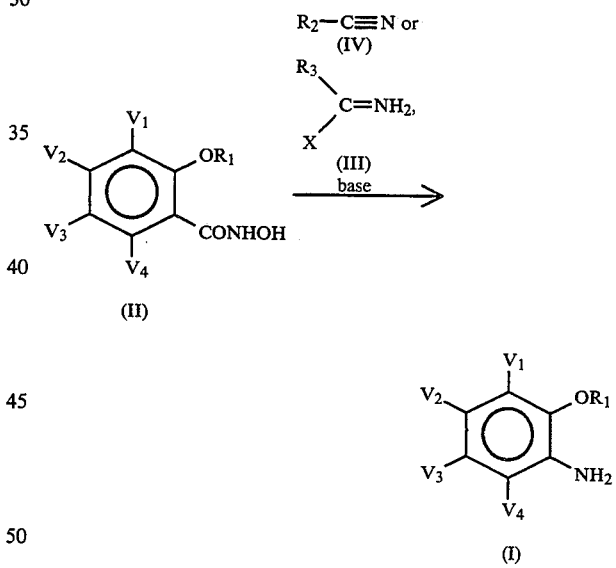

In the above formulae, $V_1$, $V_2$, $V_3$, $V_4$, $R_1$, $R_2$, $R_3$ and X have the same meanings as described hereinbefore, respectively.

In the reaction shown above, it is desirable that the nitrile represented by formula (III) or the nitrile equivalent represented by formula (IV) be used in an amount of about at least 0.02 mole per 1 mole of the compound represented by formula (II). When the group represented by $R_2$ in the nitrile of formula (III) is an alkyl group (e.g., methyl, ethyl), it is particularly preferable that a large excess of nitrile over the compound (II) be used so that the nitrile may serve for a solvent as well. When the nitrile containing as $R_2$ an aryl group (e.g., phenyl, nitrophenyl) or the nitrile equivalent (IV) is used, it is desirable that said nitrile or nitrile equivalent be used in an amount of about 0.2 to about 2.0 moles, particularly about 0.5 to about 1.0 mole, per mole of the compound (II).

Examples of the base which can be used in the present invention include alkolates (e.g., sodium methylate and potassium t-butoxide), metal carbonates (e.g., potassium carbonate and sodium carbonate), metal hydroxides (e.g., sodium hydroxide and potassium hydroxide), and organic bases (e.g., 1,8-diazabicyclo[5.4.0]undec-7-ene (DBU) and tetramethylguanidine). Of these, sodium methylate, potassium carbonate, DBU, and tetramethylguanidine are preferred. It is desirable for these bases to be used in an amount of about 0.02 to about 2.0 moles, preferably about 0.2 to about 1.0 mole, per mole of the compound (II).

The reaction temperature ranges preferably from about 25° C. to about 100° C., particularly preferably about 40° C. to about 80° C.

Suitable examples of a solvent used in the reaction include alcohols (such as methanol, ethanol, isopropyl alcohol, etc.), ethers (such as tetrahydrofuran, 1,4-dioxane, etc.), water, acetonitrile, amides (such as N,N-dimethylformamide) and so on.

It is desirable that the reaction be run under proper agitation.

Isolation and purification of the present reaction's products can be carried out using a conventional technique, such as distillation, recrystallization, chromatography (liquid chromatography) or the like.

Specific examples of compounds represented by formula (I) which are prepared in accordance with the present method are illustrated below. Additionally, specific examples of the compounds represented by formula (II) correspond to the following specific examples through replacement of —NH₂ by —CONHOH.

In the following formulas the notation "(n)" indicates a "normal" configuration for the noted hydrocarbon moiety.

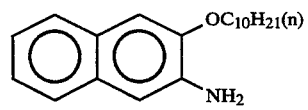

Compound 1

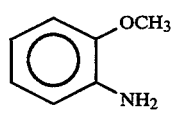

Compound 2

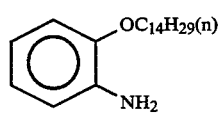

Compound 3

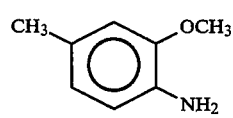

Compound 4

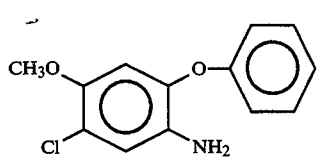

Compound 5

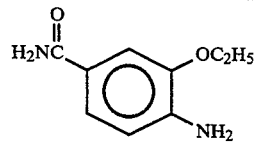

Compound 6

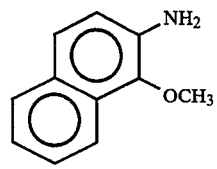

Compound 7

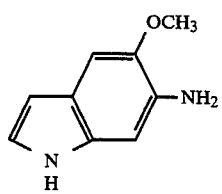

Compound 8

Specific examples of compounds of formula (III) are illustrated below.

Compound 9

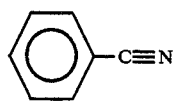

Compound 10

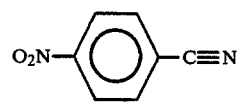

Compound 11

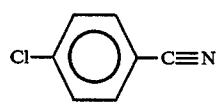

Compound 12

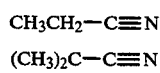

Compound 13

Compound 14

Specific examples of compounds of formula (IV) are illustrated below.

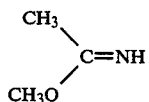

Compound 15

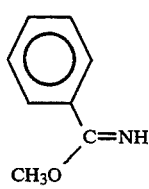

Compound 16

In accordance with the method of the present invention, aromatic amine derivatives represented by formula (I) can be produced in a high yield using inexpensive reagents under mild conditions, with less steps than is required using conventional methods.

Now, the present invention is illustrated in more detail by reference to the following examples.

EXAMPLE 1

Synthesis Example (1) of Compound 1

(i) Synthesis of Sodium 3-Decyloxy-2-naphthalenehydroxamate

To a solution containing 149 g of hydroxylamine hydrochloride in 1.5 l of methanol was added 410 ml of sodium methylate (28 wt % methanol solution). The mixture was stirred for 1 hour. The thus produced white crystals of sodium chloride was filtered out, and then the filtrate was admixed with a suspension containing 507 g of 3-decyloxy-2-naphthoic acid methyl ester in 500 ml of methanol. To the mixture, 410 ml of sodium methylate (28 wt % methanol solution) was further added dropwise over a 30-minute period. The stirring was continued for an additional 2 hours, and then the reaction mixture was allowed to stand for one night at room temperature. The thus precipitated white crystals were filtered off, thereby giving 510 g of sodium 3-decyloxy-2-naphthalenehydroxamate in a 94% yield. m.p. 109°–112° C.

(ii) Synthesis of 3-Decyloxy-2-naphthylamine (Compound 1)

Two liter of acetonitrile was added to 510 g of sodium 3-decyloxy-2-naphthalenehydroxamate obtained above, and stirred for about 30 minutes at 60° C. Thereupon, evolution of carbon dioxide gas was confirmed. The reaction mixture was further stirred with heating for 1 hour. Then, the insoluble matter (3,3'-didecyloxy-2-2'-dinaphthylurea) was filtered out, and the filtrate was concentrated. The residue was dissolved in 1 liter of ethyl acetate, and washed 3 times with 500 ml of water. The organic layer was separated from the aqueous layer, dried with Glauber's salt, and then concentrated. Thus, 323 g of whitish orange 3-decyloxy-2-naphthylamine (Compound 1) was obtained in a 84% yield. The melting point of the product was 64°–65.5° C.

EXAMPLE 2

Synthesis Example (2) of Compound 1

To a solution containing 1 g of 3-decyloxy-2-naphthalenehydroxamic acid, which was obtained by neutralizing the sodium salt synthesized in the manner described in (i) of Example 1, in 10 ml of tetrahydrofuran were added 150 mg (0.5 mole per mole of the hydroxamic acid) of benzonitrile and 110 ml (0.2 mole per mole of the hydroxamic acid) of sodium methylate (28 wt % methanol solution). The mixture was kept at 60° C. for 2 hours to effect the reaction (the formation rate of the desired Compound 1 in this reaction system was 99.2% when determined by high-speed liquid chromatography). The resulting solution was admixed with 50 ml of ethyl acetate, and washed with successive, a 50 ml portion of saturated brine and two 50 ml portions of water. The organic layer was separated from the aqueous layer, dried with Glauber's salt, and then concentrated. Thus, 850 g of 3-decyloxy-2-naphthylamine (Compound 1) was obtained in a yield of 98.0%. The thus obtained product had the same melting point as the product obtained in Example 1.

EXAMPLE 3

Synthesis of Compound 3

2-Myristyloxybenzohydroxamic acid was synthesized according to the method provided in part (i) of Example 1. Thereafter, one gram of said compound was dissolved in 5 ml of tetrahydrofuran, and thereto were added 0.83 ml of sodium methylate (28 wt % methanol solution) and 20 ml of acetonitrile. The mixture was heated to 60° C. and kept there for 1.5 hours with stirring (the formation rate of the desired compound in this reaction system was found to be 100% by an analysis using high-speed liquid chromatography). The resulting solution was admixed with 50 ml of ethyl acetate, and washed once with 50 ml of saturated brine and then twice with water. The organic layer was separated from the aqueous layer, dried with Glauber's salt, and then concentrated. The residue was admixed with 5 ml of methanol, and cooled in an ice bath to precipitate white crystals. These white crystals were filtered off, washed with 0.5 ml of ice-cold methanol, and then dried. Thus, 400 mg of 2-myristyloxyaniline (Compound 3) was obtained in a 67% yield. The melting point thereof was 45.5°–46.5° C.

EXAMPLES 4 TO 10

Compound 1 was synthesized using various catalysts (the compounds represented by general formula (III) or (IV)) and bases set forth in Table 1 in accordance with the reaction method described in Example 2. The results obtained are also shown in Table 1. Additionally, the reaction conditions (except those regarding the catalyst and the base) and the after-treatment manner adopted herein were the same as those described in Example 2.

TABLE 1

| | Catalyst | Base | Yield (%) |
|---|---|---|---|
| Example 4 | Compound 10 (1.0)*1) | DBU*2) (0.5) | 96 |
| Example 5 | Compound 10 (1.0) | K$_2$CO$_3$ (0.5) | 95 |
| Example 6 | Compound 11 (0.05) | NaOCH$_3$ (0.2) | 82 |
| Example 7 | Compound 13 (large excess) | NaOCH$_3$ (1.0) | 70 |
| Example 8 | Compound 14 (large excess) | NaOCH$_3$ (1.0) | 58 |
| Example 9 | Compound 15 (1.0) | NaOCH$_3$ (1.0) | 98 |
| Example 10 | Compound 15 (1.0) | K$_2$CO$_3$ (1.0) | 97 |

*1)Each value in parentheses in the catalyst and base columns is the number of moles per mole of hydroxamic acid.
*2)DBU is the abbreviation of diazabicycloundecene.

While the invention has been described in detail and with reference to specific embodiments thereof, it will be apparent to one skilled in the art that various changes and modifications can be made therein without departing from the spirit and scope thereof.

What is claimed is:

1. A method of producing aromatic amine derivatives represented by the following formula (I), which comprises: reacting an aromatic hydroxamic acid derivative represented by the following formula (II) in the presence of a base with a nitrile represented by the following formula (III) or a nitrile equivalent represented by the following formula (IV);

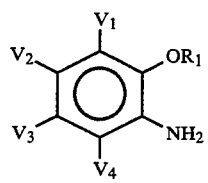

(I)

wherein in formula (I) R₁ represents an optionally substituted alkyl group, an optionally substituted alkenyl group, an optionally substituted alkynyl group or an optionally substituted aryl group; and V₁, V₂, V₃ and V₄ each represent a hydrogen atom or a group which can be substituted for a hydrogen on an aromatic ring, or V₁ and V₂, V₂ and V₃, or V₃ and V₄ combine with each other to complete a condensed ring;

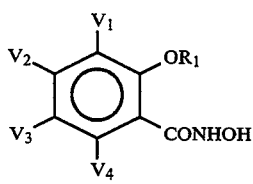

(II)

wherein in formula (II) R₁, V₁, V₂, V₃ and V₄ have the same meanings as defined in general formula (I), respectively;

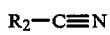

(III)

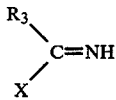

(IV)

wherein in formula (III) R₂ represents an optionally substituted alkyl group or an optionally substituted aryl group; and wherein in formula (IV) R₃ represents an optionally substituted alkyl group or an optionally substituted aryl group, and X represents an alkoxy group, an aryloxy group or a halogen atom.

2. The method of producing an aromatic amine derivative as recited in claim 1, wherein the rearrangement reaction proceeds at a temperature of from about 25° C. to about 100 ° C.

3. The method of producing an aromatic amine derivative as recited in claim 1, wherein:
the nitrile of formula (III) or the nitrile equivalent of formula (IV) is present in an amount of least about 0.02 mole per 1 mole of the aromatic hydroxamic acid derivative of Formula (II); and
the base is present in an amount of about 0.02 to about 2.0 moles per 1 mole of the aromatic hydroxamic acid derivative of formula (II).

4. The method of producing an aromatic amine derivative as recited in claim 1, wherein the nitrile of formula (III) is present.

5. The method of producing an aromatic amine derivative as recited in claim 4, wherein the R₂ group on the nitrile of formula (III) is an alkyl group, the nitrile of formula (III) is present in a large excess to the aromatic hydroxamic acid derivative of Formula (II), and the nitrile of formula (III) serves as a solvent in the method.

6. The method of producing an aromatic amine derivative as recited in claim 4, wherein the R₂ group on the nitrile of formula (III), is an aryl group, and the nitrile of formula (III) is present in an amount of about 0.2 to about 2.0 moles per 1 mole of the aromatic hydroxamic acid derivative of formula (II).

7. The method of producing an aromatic amine derivative as recited in claim 1, wherein the nitrile equivalent of formula (IV) is present.

8. The method of producing an aromatic amine derivative as recited in claim 7, wherein the nitrile equivalent of formula (IV) is present is an amount of about 0.2 to about 2.0 moles per 1 mole of the aromatic hydroxamic acid derivative of formula (II).

9. The method of producing an aromatic amine derivative as recited in claim 1, wherein said base is selected from the group consisting of sodium methylate, potassium carbonate, diazabicycloundecane and 1,1,3,3-tetramethylguanidine.

10. The method of producing an aromatic amine derivative as recited in claim 1, wherein:
R₁ is a straight-chain, branched-chain, or cyclic $C_{1-32}$ alkyl group, $C_{2-32}$ alkenyl group, or $C_{2-32}$ alkynyl group, any of which may be optionally substituted by a substituent selected from the group consisting of:
a halogen atom, an alkoxy group, an aryloxy group, a heteroxcycloxy group, an acyloxy group, an alkyl group, an alkenyl group, an alkinyl group, an aryl group, an amino group, a hydroxyl group, a carbonamido group, a sulfonamide group, an ureido group, a sulfamido group, an oxycarbonamido group, a carboxyl group, a carbamoyl group, an oxycarbonyl group, a sulfo group, a sulfamoyl group, an alkylsulfonyl group, an arylsulfonyl group, a cyano group, a nitro group and a heterocyclyl group; or
R₁ is a $C_{6-20}$ aryl group which may be optionally substituted by a substituent selected from the group consisting of:
a halogen atom, an alkoxy group, an aryloxy group, a heteroxcycloxy group, an acyloxy group, an alkyl group, an alkenyl group, an alkinyl group, an aryl group, an amino group, a hydroxyl group, a carbonamido group, a sulfonamido group, an ureido group, a sulfamido group, an oxycarbonamido group, a carboxyl group, a carbamoyl group, an oxycarbonyl group, a sulfo group, a sulfamoyl group, an alkylsulfonyl group, an arylsulfonyl group, a cyano group, a nitro group and a heterocyclyl group.

11. The method of producing an aromatic amine derivative as recited in claim 1, wherein:
V₁, V₂, V₃, and V₄ are the same or different and are selected from the group consisting of:
a hydrogen atom, a halogen atom, an alkyl group, an alkenyl group, an aryl group, an alkoxy group, an aryloxy group, an acyloxy group, an amido group, a sulfonamido group, an ureido group, an alkyloxycarbonyl group, a carbamoyl group, a sulfamoyl group, a sulfonyl group, a sulfo group, a cyano group or a heterocyclyl group; or
V₁ with V₂, V₂ with V₃, or V₃ with V₄ form a condensed ring selected from the group consisting of: substituted and unsubstituted benzene, cyclopentadiene, tropilidene, pyridine, furan, thiophene, pyrrole, thiazole, oxazole, imidazole and triazole.

12. The method of producing an aromatic amine derivative as recited in claim 1, wherein:
R₂ is selected from the group consisting of: methyl, phenyl and p-nitrophenyl; and R3 is selected from the group consisting of: methyl, phenyl and p-nitrophenyl.

13. The method of producing an aromatic amine derivative as recited in claim 1, wherein X is selected from the group consisting of methoxy, phenoxy and chlorine.

14. The method of producing an aromatic amine derivative of formula (I) as recited in claim 1, wherein the formula (I) aromatic amine derivative is selected from the group consisting of:

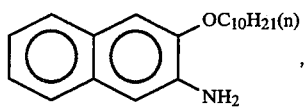

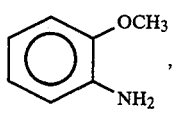

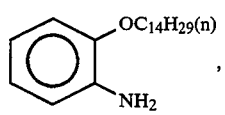

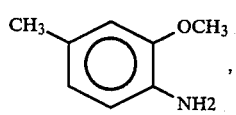

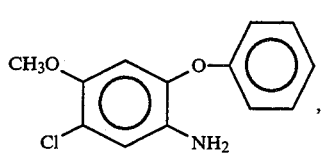

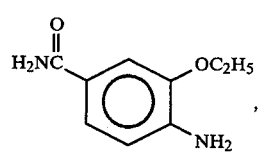

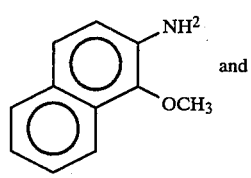

and

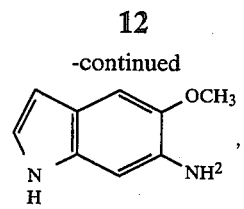

15. The method of producing an aromatic amine derivative as recited in claim 1, wherein the nitrile of formula (III) is selected from the group consisting of:

$$CH_3-C \equiv N,$$

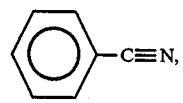

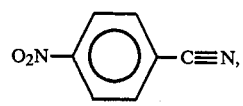

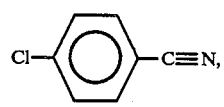

and $$CH_3CH_2-C \equiv N.$$

16. The method of producing an aromatic amine derivative as recited in claim 1, wherein the nitrile equivalent of formula (IV) is selected from the group consisting of:

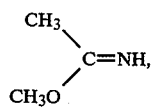

and

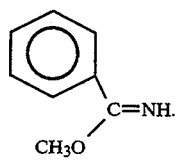

17. The method of producing an aromatic amine derivative as recited in claim 1, wherein R2 and R3 are the same or different and are selected from the group consisting of an optionally substituted alkyl group having 1 to 10 carbon atoms, and an optionally substituted aryl group having 6-22 carbon atoms.

* * * * *